US00PP11928P2

(12) United States Plant Patent
Strope

(10) Patent No.: US PP11,928 P2
(45) Date of Patent: Jun. 12, 2001

(54) PETUNIA PLANT NAMED 'BALRUFPURP'

(75) Inventor: Kerry Strope, Pismo Beach, CA (US)

(73) Assignee: Ball FloraPlant, a division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 09/475,951

(22) Filed: Dec. 31, 1999

(51) Int. Cl.[7] ..... A01H 5/00
(52) U.S. Cl. ..... Plt./356
(58) Field of Search ..... Plt./356

*Primary Examiner*—Bruce R. Campell
*Assistant Examiner*—June Hwu
(74) *Attorney, Agent, or Firm*—C. A. Whealy

(57) ABSTRACT

A new and distinct cultivar of Petunia plant named 'Balrufpurp', characterized by its large red purple double flowers; mounded and eventually semi-trailing plant habit; and freely basal-branching habit.

2 Drawing Sheets

BACKGROUND OF THE INVENTION

The present invention relates to a new and distinct cultivar of Double Petunia plant, botanically known as *Petunia× hybrida,* and hereinafter referred to by the cultivar name Balrufpurp.

The new Petunia is a product of a planned breeding program conducted by the Inventor in Arroyo Grande, Calif. The objective of the breeding program was to develop new Petunia cultivars with large double flowers; freely-branching vigorous growth habit; and attractive flower and foliage colors.

The new Petunia originated by exposing plants of an unidentified selection of *Petunia×hybrida* described as a double white-flowered selection to the mutagen colchicine. Following the treatment, cuttings were harvested from the treated plants and the cuttings were rooted and flowered. The new Petunia was discovered and selected by the Inventor as a single flowering plant within this population in Arroyo Grande in 1998. The selection of this plant was based on its attractive flower color and semi-double flower form.

Asexual reproduction of the new cultivar by terminal cuttings taken at Arroyo Grande has shown that the unique features of this new Petunia are stable and reproduced true to type in successive generations of asexual reproduction.

SUMMARY OF THE INVENTION

The following traits have been repeatedly observed and are determined to be the unique characteristics of 'Balrufpurp'. These characteristics in combination distinguish 'Balrufpurp' as a new and distinct cultivar:

1. Large red purple double flowers.

2. Mounded and eventually semi-trailing plant habit.

3. Freely basal-branching habit.

The new Petunia can be compared to the cultivar, Cascadia Double Pink, not patented. However, in side-by-side comparisons conducted by the Inventor in Arroyo Grande, plants of the new Petunia differ from plants of the cultivar Cascadia Double Pink in the following characteristics:

1. Plants of the new Petunia are taller than plants of the cultivar Cascadia Double Pink.

2. Plants of the new Petunia have longer and more pubescent leaves than plants of the cultivar Cascadia Double Pink.

3. Plants of the new Petunia have larger flowers than plants of the cultivar Cascadia Double Pink.

4. Flower color of plants of the new Petunia is much darker than flower color of plants of the cultivar Cascadia Double Pink.

5. Plants of the new Petunia have longer peduncles than plants of the cultivar Cascadia Double Pink.

BRIEF DESCRIPTION OF THE PHOTOGRAPHS

The accompanying photographs illustrate the overall appearance of the new cultivar as true as it is reasonably possible to obtain in colored reproductions of this type. Colors in the photographs may differ slightly from the color values cited in the detailed botanical description which accurately describe the actual colors of the new Petunia.

The photograph on the first sheet comprises a top perspective view of typical flowers and leaves of 'Balrufpurp'.

The photograph on the second sheet comprises a side perspective view of a typical flowering plant of 'Balrufpurp'.

DETAILED BOTANICAL DESCRIPTION

The cultivar Balrufpurp has not been observed under all possible environmental conditions. The phenotype may vary somewhat with variations in environment such as temperature and light intensity, without, however, any variance in genotype. The following observations and measurements describe plants about 10 weeks after planting rooted cuttings and grown in 10-cm pots in West Chicago, Ill., under commercial practice in a double-layered acrylic-covered greenhouse with day temperatures about 21° C., night temperatures about 19° C., and light levels about 2,500 to 3,500 footcandles.

In the following description, color references are made to The Royal Horticultural Society Colour Chart except where general terms of ordinary dictionary significance are used.

Botanical classification: *Petunia×hybrida* cultivar Balrufpurp.

Parentage: Induced mutation of an unidentified selection of *Petunia×hybrida* described as a double white-flowered selection, not patented.

Propagation:

*Type cutting.*—Terminal cuttings.

*Time to initiate roots.*—About 7 days with 18° C.

*Time to develop roots.*—About 21 days with 18° C.

*Root description.*—Fibrous, fine, freely branching.

Plant description:

*Form.*—Indeterminate; mounded and eventually semi-trailing.

*Growth and branching habit.*—Moderately vigorous. Freely basal-branching; typically about four lateral branches per plant; pinching enhances branching. Appropriate for 10 to 15-cm containers and hanging baskets.

*Crop time.*—About 8 to 10 weeks are required to produce a finished flowering plant from a rooted cutting.

*Plant height* (*from soil level to top of plant plane*).—About 15.4 cm.

*Area of spread.*—About 24.3 cm.

*Lateral branches.*—Length: About 12 cm. Diameter: About 4 mm. Internode length: About 1.3 cm. Texture: Pubescent. Color: Closest to 137C.

*Foliage description.*—Leaves simple, generally symmetrical and long persisting. Leaf arrangement alternate before flowering, opposite after flowering. Quantity per lateral branch: About 14. Length: About 4.5 cm. Width: About 2.5 cm. Shape: Elliptic. Apex: Rounded. Base: Attenuate. Margin: Entire. Texture: Pubescent on both surfaces, velvety; viscid. Color: Young and mature foliage, upper surface: 137A. Young and mature foliage, lower surface: 137C. Venation, both surfaces: 137D. Petiole: Length: About 3 mm. Diameter: About 2 mm. Color: 137D.

Flower description:

*Flower type and habit.*—Red purple, double flowers; salverform; flowers face outward; single, axillary. Flowers persistent. Flowering continuous. Not fragrant.

*Natural flowering season.*—Long day responsive; flowering from spring through fall.

*Flower buds* (*showing color*).—Length: About 2.2 cm. Diameter: About 1 cm. Shape: Funnel-shaped.

*Corolla.*—Arrangement/appearance: Outer whorl of about five petals, fused into a flared trumpet, ruffled, typically more than 25 inner petaloids; petaloids irregular in shape and size. Flower diameter: About 6.9 cm. Flower tube length: About 5.4 cm. Flower throat diameter, distal end: About 1.7 cm. Flower tube diameter, proximal end: About 9 mm. Petal length from throat: About 3.4 cm. Petal width: About 2.7 cm. Petal shape; Roughly spatulate, fan-shaped. Petal apex: Rounded, wavy. Petal margin: Entire to somewhat dentate. Texture: Smooth to slightly rugose; velvety. Color: Petal, upper surface, opened flower: Between 72A and 77A fading to 90A with development; veins, 86A. Petal, lower surface, opened flower: 88C; veins, 145B. Flower throat (inside): 155C; veins, 86A. Flower tube (outside): 77D; veins, 145B.

*Sepals.*—Quantity/arrangement: Five; not imbricate. Shape: Linear. Apex: Rounded. Margin: Entire. Aspect: Upright. Texture: Smooth, velvety. Color, both surfaces: 139A.

*Peduncle.*—Strength: Moderately strong. Angle: About 45° to stem. Length: About 3 cm. Color: Close to 137C.

*Reproductive organs.*—Stamens: Anther shape: Oval. Anther length: About 2 mm. Anther color: 103C. Pollen amount: Abundant. Pollen color: 115C. Pistils: Pistil length: About 1.3 cm. Style color: 150B. Stigma color: 150C. Ovary color: 150A.

*Seed.*—Seed production has not been observed.

Disease resistance: Plants of the new Petunia have not been observed to be resistant to pathogens common to Petunia.

It is claimed:

1. A new and distinct cultivar of Petunia plant named 'Balrufpurp', as illustrated and described.

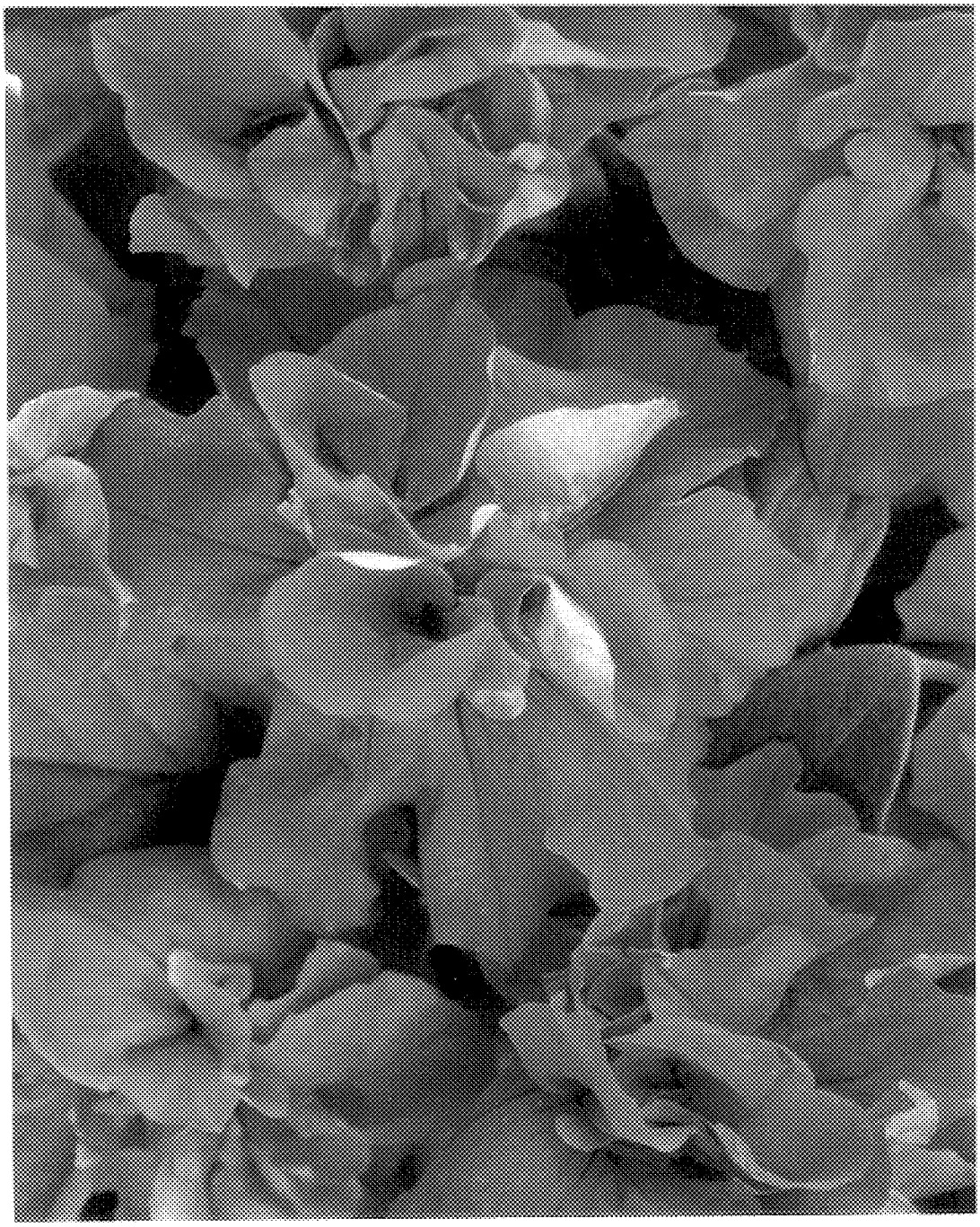

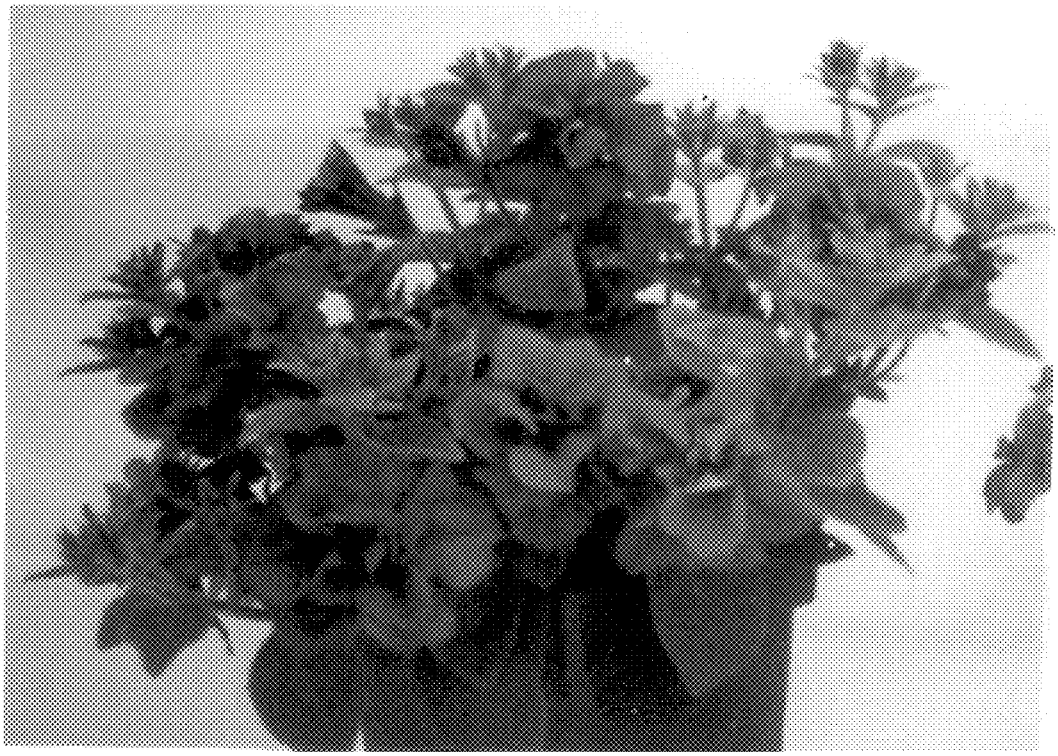

* * * * *